US010881840B2

(12) United States Patent
Hobson et al.

(10) Patent No.: US 10,881,840 B2
(45) Date of Patent: *Jan. 5, 2021

(54) INFLATABLE IMBIBED POLYMER DEVICES

(71) Applicant: W. L. Gore & Associates, Inc., Newark, DE (US)

(72) Inventors: Alex R. Hobson, Flagstaff, AZ (US); Michael Houghton, Newark, DE (US); David R. King, Lake Como, NJ (US); Joseph E. Korleski, Jr., Newark, DE (US); Brian C. Lentz, Newark, DE (US); Kenneth Newcomb, Wilmington, DE (US); Peter J. Roeber, Wallingford, PA (US); John Streeter, Flagstaff, AZ (US)

(73) Assignee: W. L. Gore & Associates, Inc., Newark, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/882,653

(22) Filed: Jan. 29, 2018

(65) Prior Publication Data

US 2018/0154121 A1   Jun. 7, 2018

Related U.S. Application Data

(60) Continuation of application No. 15/204,902, filed on Jul. 7, 2016, now Pat. No. 9,878,133, which is a (Continued)

(51) Int. Cl.
*A61M 25/10* (2013.01)
*B32B 1/08* (2006.01)
(Continued)

(52) U.S. Cl.
CPC .......... *A61M 25/1029* (2013.01); *A61F 2/958* (2013.01); *A61F 7/123* (2013.01); (Continued)

(58) Field of Classification Search
CPC .......... A61M 25/1002; A61M 25/1006; A61M 25/1025; A61M 25/1027; A61M 25/1029; A61M 25/1034; B32B 1/08
See application file for complete search history.

(56) References Cited

U.S. PATENT DOCUMENTS 1,690,995 A   11/1928 Pratt
3,640,282 A   2/1972 Kamen
(Continued)

FOREIGN PATENT DOCUMENTS

EP   0372088 A4   1/1991
EP   0540858 A1   5/1993
(Continued)

OTHER PUBLICATIONS

Dillon M E, Silicone and Poly (tetrafluoroethylene) Interpenetrating Polymer Networks, 1994 American Chemical Society, Only first three lines of abstract have been presented (an incomplete abstract has been presented).

*Primary Examiner* — Walter Aughenbaugh

(57) ABSTRACT

The present invention provides a stretchable material suitable for use in an inflatable medical device. The stretchable material has at least one reinforcing polymer layer with a top and bottom side forming a porous matrix which is imbibed with a sealing material to infiltrate and substantially seal spaces of the porous matrix and extend beyond the reinforcing polymer layer to form a surface coating.

12 Claims, 10 Drawing Sheets

Related U.S. Application Data continuation of application No. 14/918,845, filed on Oct. 21, 2015, now abandoned, which is a division of application No. 11/500,794, filed on Aug. 7, 2006, now Pat. No. 9,180,279.

(51) Int. Cl.
*A61F 2/958* (2013.01)
*A61L 29/08* (2006.01)
*C08J 7/04* (2020.01)
*A61L 29/12* (2006.01)
*A61L 29/14* (2006.01)
*A61F 7/12* (2006.01)
*A61L 29/04* (2006.01)
*B32B 1/00* (2006.01)
*B32B 1/02* (2006.01)
*B32B 5/18* (2006.01)

(52) U.S. Cl.
CPC ........... *A61L 29/041* (2013.01); *A61L 29/085* (2013.01); *A61L 29/126* (2013.01); *A61L 29/146* (2013.01); *A61M 25/10* (2013.01); *A61M 25/1002* (2013.01); *A61M 25/104* (2013.01); *A61M 25/1006* (2013.01); *A61M 25/1018* (2013.01); *A61M 25/1025* (2013.01); *A61M 25/1027* (2013.01); *A61M 25/1034* (2013.01); *A61M 25/10184* (2013.11); *B32B 1/08* (2013.01); *C08J 7/0427* (2020.01); *A61F 2007/126* (2013.01); *A61F 2250/0067* (2013.01); *A61M 2025/105* (2013.01); *A61M 2025/1031* (2013.01); *A61M 2025/1052* (2013.01); *A61M 2025/1075* (2013.01); *A61M 2205/0216* (2013.01); *B32B 1/00* (2013.01); *B32B 1/02* (2013.01); *B32B 5/18* (2013.01); *C08J 2327/18* (2013.01); *C08J 2475/04* (2013.01); *Y10T 428/1352* (2015.01); *Y10T 428/1386* (2015.01)

(56) References Cited

U.S. PATENT DOCUMENTS

| | | |
|---|---|---|
| 3,746,003 A | 7/1973 | Blake |
| 3,953,566 A | 4/1976 | Gore |
| 4,003,382 A | 1/1977 | Dyke |
| 4,106,509 A | 8/1978 | McWhorter |
| 4,187,390 A | 2/1980 | Gore |
| 4,194,041 A | 3/1980 | Gore et al. |
| 4,279,245 A | 7/1981 | Takagi et al. |
| 4,280,500 A | 7/1981 | Ono |
| 4,304,010 A | 12/1981 | Mano |
| 4,327,736 A | 5/1982 | Inoue |
| 4,338,942 A | 7/1982 | Fogarty |
| 4,403,612 A | 9/1983 | Fogarty |
| 4,443,511 A | 4/1984 | Worden et al. |
| 4,490,421 A | 12/1984 | Levy |
| 4,573,966 A | 3/1986 | Weikl |
| 4,596,839 A | 6/1986 | Peters |
| 4,608,984 A | 9/1986 | Fogarty |
| 4,613,544 A | 9/1986 | Burleigh |
| 4,619,641 A | 10/1986 | Schanzer |
| 4,637,396 A | 1/1987 | Cook |
| 4,650,466 A | 3/1987 | Luther |
| 4,702,252 A | 10/1987 | Brooks |
| 4,706,670 A | 11/1987 | Andersen |
| 4,713,070 A | 12/1987 | Mano |
| 4,737,219 A | 4/1988 | Taller |
| 4,739,762 A | 4/1988 | Palmaz |
| 4,743,480 A | 5/1988 | Campbell et al. |
| 4,764,560 A | 8/1988 | Mitchell |
| 4,816,339 A | 3/1989 | Tu et al. |
| 4,819,751 A | 4/1989 | Shimada |
| 4,832,688 A | 5/1989 | Sagae |
| 4,896,669 A | 1/1990 | Bhate |
| 4,946,464 A | 8/1990 | Pevsner |
| 4,955,899 A | 9/1990 | Della Coma et al. |
| 5,041,047 A | 8/1991 | Casale |
| 5,061,276 A | 10/1991 | Tu et al. |
| 5,066,298 A | 11/1991 | Hess |
| 5,071,609 A | 12/1991 | Tu et al. |
| 5,087,244 A | 2/1992 | Wolinsky |
| 5,100,429 A | 3/1992 | Sinofsky |
| 5,108,370 A | 4/1992 | Walinsky |
| 5,112,304 A | 5/1992 | Barlow |
| 5,116,318 A | 5/1992 | Hillstead |
| 5,137,512 A | 8/1992 | Burns |
| 5,147,302 A | 9/1992 | Euteneuer |
| 5,152,782 A | 10/1992 | Kowligi et al. |
| 5,171,297 A | 12/1992 | Barlow |
| 5,192,296 A | 3/1993 | Bhate |
| 5,195,970 A | 3/1993 | Gahara |
| 5,197,978 A | 3/1993 | Hess |
| 5,201,706 A | 4/1993 | Noguchi |
| 5,211,654 A | 5/1993 | Kaltenbach |
| 5,213,576 A | 5/1993 | Abiuso et al. |
| 5,226,880 A | 7/1993 | Martin |
| 5,236,659 A | 8/1993 | Pinchuk |
| 5,254,090 A | 10/1993 | Lombardi |
| 5,256,143 A | 10/1993 | Miller |
| 5,286,254 A | 2/1994 | Shapland |
| 5,290,306 A | 3/1994 | Trotta |
| 5,304,120 A | 4/1994 | Crandell |
| 5,304,214 A | 4/1994 | DeFord |
| 5,304,340 A | 4/1994 | Downey |
| 5,308,356 A | 5/1994 | Blackshear |
| 5,330,429 A | 7/1994 | Noguchi |
| 5,338,299 A | 8/1994 | Barlow |
| 5,342,305 A | 8/1994 | Shonk |
| 5,342,348 A | 8/1994 | KAplan |
| 5,348,538 A | 9/1994 | Wang |
| 5,358,486 A | 10/1994 | Saab |
| 5,358,516 A | 10/1994 | Myers et al. |
| 5,366,442 A | 11/1994 | Wang |
| 5,366,472 A | 11/1994 | Hillstead |
| 5,370,618 A | 12/1994 | Leonhardt |
| 5,403,340 A | 4/1995 | Wang |
| 5,409,495 A | 4/1995 | Osborn |
| 5,415,636 A | 5/1995 | Forman |
| 5,425,710 A | 6/1995 | Khair |
| 5,429,605 A | 7/1995 | Richling |
| 5,456,661 A | 10/1995 | Narciso |
| 5,458,568 A | 10/1995 | Racchini et al. |
| 5,458,605 A | 10/1995 | Klemm |
| 5,466,252 A | 11/1995 | Soukup et al. |
| 5,470,313 A | 11/1995 | Crocker et al. |
| 5,470,314 A | 11/1995 | Walinsky |
| 5,476,589 A | 12/1995 | Bacino |
| 5,478,320 A | 12/1995 | Trotta |
| 5,478,349 A | 12/1995 | Nickolas |
| 5,484,411 A | 1/1996 | Inderbitzen et al. |
| 5,490,839 A | 2/1996 | Wang |
| 5,496,276 A | 3/1996 | Wang |
| 5,498,238 A | 3/1996 | Shapland |
| 5,499,973 A | 3/1996 | Saab |
| 5,499,980 A | 3/1996 | Euteneuer |
| 5,499,995 A | 3/1996 | Teirstein |
| 5,500,180 A | 3/1996 | Anderson |
| 5,500,181 A | 3/1996 | Wang |
| 5,512,051 A | 4/1996 | Wang et al. |
| 5,519,172 A | 5/1996 | Spencer |
| 5,527,282 A | 6/1996 | Segal |
| 5,529,820 A | 6/1996 | Nomi et al. |
| 5,571,089 A | 11/1996 | Crocker |
| 5,599,307 A | 2/1997 | Bacher |
| 5,609,605 A | 3/1997 | Marshall |
| 5,613,979 A | 3/1997 | Trotta |
| 5,620,649 A | 4/1997 | Trotta |
| 5,641,373 A | 6/1997 | Shannon et al. |
| 5,645,560 A | 7/1997 | Crocker |
| 5,647,848 A | 7/1997 | Jorgensen |
| 5,681,522 A | 10/1997 | Roychowdhury |

(56) References Cited

U.S. PATENT DOCUMENTS

| | | | |
|---|---|---|---|
| 5,695,469 A | 12/1997 | Segal | |
| 5,716,340 A | 2/1998 | Schweich | |
| 5,716,396 A | 2/1998 | Williams | |
| 5,752,934 A * | 5/1998 | Campbell | A61L 29/085 604/96.01 |
| 5,766,201 A | 6/1998 | Ravenscroft et al. | |
| 5,797,877 A | 8/1998 | Hamilton | |
| 5,807,327 A | 9/1998 | Green | |
| 5,843,116 A | 12/1998 | Crocker et al. | |
| 5,868,704 A | 2/1999 | Campbell et al. | |
| 5,868,708 A | 2/1999 | Hart | |
| 5,893,840 A | 4/1999 | Hull | |
| 5,908,406 A | 6/1999 | Ostapchenko | |
| 5,931,851 A | 8/1999 | Morales | |
| 5,944,734 A | 8/1999 | Hermann | |
| 5,948,345 A | 9/1999 | Patel et al. | |
| 5,951,941 A | 9/1999 | Wang | |
| 5,954,745 A | 9/1999 | Gertler et al. | |
| 5,972,441 A | 10/1999 | Campbell et al. | |
| 6,010,480 A | 1/2000 | Abele | |
| 6,013,092 A | 1/2000 | Dehdashtian | |
| 6,027,779 A | 2/2000 | Campbell et al. | |
| 6,048,356 A | 4/2000 | Ravenscroft | |
| 6,063,092 A | 5/2000 | Shin | |
| 6,074,381 A | 6/2000 | Dinh et al. | |
| 6,120,477 A | 9/2000 | Campbell et al. | |
| 6,132,824 A | 10/2000 | Hamlin | |
| 6,234,995 B1 | 5/2001 | Peacock | |
| 6,287,290 B1 | 9/2001 | Perkins | |
| 6,287,314 B1 | 9/2001 | Lee | |
| 6,319,249 B1 | 11/2001 | Tollner | |
| 6,319,259 B1 | 11/2001 | Lee | |
| 6,319,529 B1 | 11/2001 | Thompson | |
| 6,336,937 B1 | 1/2002 | Vonesh et al. | |
| 6,344,045 B1 * | 2/2002 | Lim | A61F 2/958 606/108 |
| 6,375,637 B1 | 4/2002 | Campbell et al. | |
| 6,428,506 B1 | 8/2002 | Simhambhatla et al. | |
| 6,482,348 B1 | 11/2002 | Wang | |
| 6,488,688 B2 | 12/2002 | Lim | |
| 6,572,813 B1 | 6/2003 | Zhang | |
| 6,602,224 B1 | 8/2003 | Simhambhatla | |
| 6,663,646 B1 | 12/2003 | Shah | |
| 6,746,425 B1 | 6/2004 | Beckham | |
| 6,756,094 B1 | 6/2004 | Wang et al. | |
| 6,841,029 B2 | 1/2005 | Lim | |
| 6,887,227 B1 | 5/2005 | Barbut | |
| 6,890,395 B2 | 5/2005 | Simhambhatla | |
| 6,905,743 B1 | 6/2005 | Chen et al. | |
| 6,923,827 B2 | 8/2005 | Campbell et al. | |
| 6,939,593 B2 | 9/2005 | Wang | |
| 6,946,173 B2 | 9/2005 | Lim | |
| 6,977,103 B2 | 12/2005 | Chen | |
| 7,052,507 B2 | 5/2006 | Wakuda | |
| 7,195,638 B1 | 3/2007 | Sridharan | |
| 7,279,208 B1 | 10/2007 | Goffena | |
| 7,306,729 B2 | 12/2007 | Bacino et al. | |
| 7,625,337 B2 | 12/2009 | Campbell | |
| 7,785,290 B2 | 8/2010 | Alpini et al. | |
| 7,892,201 B1 | 2/2011 | Laguna et al. | |
| 9,180,279 B2 * | 11/2015 | Hobson | A61L 29/126 |
| 9,808,605 B2 * | 11/2017 | Bacino | A61L 29/146 |
| 9,878,133 B2 * | 1/2018 | Hobson | A61M 25/104 |
| 2001/0008970 A1 | 7/2001 | Ravenscroft | |
| 2001/0043998 A1 | 11/2001 | Chen et al. | |
| 2002/0087165 A1 | 7/2002 | Lee | |
| 2002/0161388 A1 | 10/2002 | Samuels et al. | |
| 2002/0163104 A1 | 11/2002 | Motsenbocker | |
| 2003/0074016 A1 | 4/2003 | Campbell | |
| 2003/0083687 A1 | 5/2003 | Paliazza | |
| 2003/0088209 A1 | 5/2003 | Chiu | |
| 2003/0130716 A1 | 7/2003 | Weber | |
| 2003/0211258 A1 | 11/2003 | Sridharan et al. | |
| 2004/0015183 A1 | 1/2004 | Lim | |
| 2004/0082965 A1 | 4/2004 | Beckham | |
| 2004/0143287 A1 | 7/2004 | Konstantino et al. | |
| 2004/0171442 A1 | 9/2004 | Lim | |
| 2004/0199202 A1 | 10/2004 | Dubrul | |
| 2004/0230309 A1 | 11/2004 | DiMauro et al. | |
| 2004/0254625 A1 | 12/2004 | Stephens | |
| 2005/0015048 A1 | 1/2005 | Chiu | |
| 2005/0038503 A1 | 2/2005 | Greenhalgh | |
| 2005/0267409 A1 | 12/2005 | Shkolnik | |
| 2005/0273152 A1 | 12/2005 | Campbell et al. | |
| 2006/0085024 A1 | 4/2006 | Pepper | |
| 2006/0136032 A1 | 6/2006 | Legarda et al. | |
| 2006/0161102 A1 | 7/2006 | Newcomb | |
| 2006/0271091 A1 | 11/2006 | Campbell et al. | |
| 2007/0055301 A1 | 3/2007 | Campbell | |
| 2007/0061000 A1 | 3/2007 | Campbell | |
| 2007/0219489 A1 | 9/2007 | Johnson | |
| 2008/0125711 A1 | 5/2008 | Alpini et al. | |
| 2008/0140173 A1 | 6/2008 | Eskaros et al. | |
| 2008/0255507 A1 | 10/2008 | Mushtaha | |
| 2008/0257155 A1 | 10/2008 | Bacino | |
| 2008/0312730 A1 | 12/2008 | Campbell | |
| 2009/0032470 A1 | 2/2009 | Bacino | |
| 2009/0053103 A1 | 2/2009 | Mortimer | |
| 2009/0283206 A1 | 11/2009 | Eskaros et al. | |
| 2010/0049123 A1 | 2/2010 | Alpini et al. | |
| 2010/0262178 A1 | 10/2010 | Alpini | |

FOREIGN PATENT DOCUMENTS

| | | |
|---|---|---|
| EP | 0737488 A1 | 10/1996 |
| EP | 0769307 A3 | 1/1998 |
| EP | 0829269 A1 | 3/1998 |
| EP | 0628586 B1 | 11/1998 |
| EP | 0540585 B1 | 8/2001 |
| GB | 1566674 A | 8/1980 |
| NL | 1008178 C2 | 4/1999 |
| WO | WO-1990014054 A1 | 11/1990 |
| WO | WO-1994002185 A1 | 2/1994 |
| WO | WO-1996014895 A1 | 5/1994 |
| WO | WO-1995005555 A1 | 2/1995 |
| WO | WO-1995009667 A1 | 4/1995 |
| WO | WO-1995017920 A1 | 7/1995 |
| WO | WO-1996040350 A1 | 12/1996 |
| WO | WO-1997002791 A1 | 1/1997 |
| WO | WO-1997040877 A1 | 11/1997 |
| WO | WO-2002068011 A1 | 9/2002 |
| WO | WO-2003000307 A1 | 1/2003 |
| WO | WO-2008021002 A1 | 2/2008 |
| WO | WO-2008021003 A1 | 2/2008 |
| WO | WO-2008021006 A3 | 2/2008 |
| WO | WO-2008021013 A1 | 2/2008 |

\* cited by examiner

INFLATABLE IMBIBED POLYMER DEVICES

CROSS-REFERENCE TO RELATED APPLICATION

This application is a continuation of U.S. patent application Ser. No. 15/204,902, filed Jul. 7, 2016, now U.S. Pat. No. 9,878,133, issued Jan. 30, 2018, which is a continuation of U.S. patent application Ser. No. 14/918,845, filed Oct. 21, 2015, which is a divisional of U.S. patent application Ser. No. 11/500,794, filed Aug. 7, 2006, now U.S. Pat. No. 9,180,279, issued Nov. 10, 2015, all of which are incorporated herein by reference in their entireties for all purposes.

BACKGROUND OF THE INVENTION

The present invention relates to a unique material suited for use in balloon catheters and, more particularly, to a low profile non-shortening wrapped balloon configured to expand to a predetermined diameter upon application of a predetermined pressure thereto. The unique properties of the material of the present invention enable wrapped balloons to be made without the use of internal bladders.

Balloon catheters are well known in the art. Such catheters are employed in a variety of medical procedures, including dilation of narrowed blood vessels, placement of stents and other implants, temporary occlusion of blood vessels, and other vascular uses.

In a typical application, the balloon is advanced to the desired location in the vascular system. The balloon is then pressure-expanded in accordance with a medical procedure. Thereafter, the pressure is removed from the balloon, allowing the balloon to contract and permit removal of the catheter. It is to be appreciated that prior art balloons are typically formed of an elastomeric material which is readily pressure-expanded, and also readily contracts upon removal of the inflation pressure.

Some catheter balloons constructed of both elastomeric and non-elastomeric materials have been described previously. U.S. Pat. No. 4,706,670 describes a balloon dilatation catheter constructed of a shaft made of an elastomeric tube and reinforced with longitudinal inelastic filaments. This device incorporates a movable portion of the shaft to enable the offset of the reduction in length of the balloon portion as the balloon is inflated. A major drawback to balloons of this type is the need for a bladder which increases the profile of the balloon.

Traditionally, a fluoropolymer matrix which is filled with a coating that does not extend outside the matrix permits the coating to pull away from the matrix causing holes that eventually demonstrate themselves in a "weeping" manner on the balloon. This is believed to be due to the inadequate adhesion strength between the matrix and the coating as well as the stress concentrations at those interfaces.

There is a need in the art for a low profile wrapped balloon which does not lengthen or shorten upon inflation and has the ability to withstand inflation pressure strain without disruption, while still remaining watertight without the use of a separate bladder that adds to the balloon profile. The present invention fulfills this need by providing a unique material which allows for the elimination of a bladder. It also allows the balloon to readily expand under pressure without leaking.

SUMMARY OF THE INVENTION

The present invention provides a stretchable material comprising a reinforcing polymer having a porous matrix with void spaces and a sealing material imbibed into the reinforcing polymer substantially sealing the porous matrix void spaces and extending beyond the reinforcing polymer matrix to form a surface coating that can be stretched without the occurrence of holes through the thickness of the material. In a preferred embodiment, a low angle wrapped catheter balloon is comprised of a material which stretches primarily in one direction and less than 54.7 degrees is formed with said material. As the balloon is inflated to its working diameter, the wrapped material rotates towards the balanced force angle of 54.7 degrees. When rotating, the wrapped material also strains perpendicular to the length of the wrap according to the following geometric relationship (Width$_F$=Width$_I$×(cos θ$_F$/cos θ$_I$)$^2$×(tan θ$_F$/tan θ$_I$) where F is Final and I is initial. This strain can exceed 500 percent in some balloons depending on the deflated to inflated diameter ratio. The present invention allows for this strain to occur without inducing holes or compromising the sealing coating. The material is suitable for liquid or gas impermeable applications.

The present invention further provides a balloon catheter comprising a tubular catheter shaft having a longitudinal axis and an inflatable bladderless wrapped balloon affixed to the catheter shaft wherein the balloon comprises at least one reinforcing polymer layer with a top and bottom side forming a porous matrix, said porous matrix is imbibed with a sealing material that infiltrates and substantially seals void spaces of the porous matrix and extends beyond the reinforcing polymer layer to form a surface coating. The surface coating is formed on at least one side of the reinforcing polymer layer.

The present invention yet further provides a balloon catheter with a surface coating thickness which is modulated to allow for controlled porosity when strained due to inflation.

DESCRIPTION OF THE DRAWINGS

FIG. 1A is the reinforcing polymer prior to imbibing. FIG. 1B shows the imbibed reinforcing polymer with two surface coatings.

DETAILED DESCRIPTION OF THE INVENTION

It has been found that a reduction in the profile of prior art balloons using elastomeric bladders and outer reinforcing materials can be achieved using the materials of the present invention. The material of the present invention combines a reinforced matrix with elastomeric properties. This unique combination allows balloons to be formed without the need for a separate elastomeric bladder, thus providing reduced profiles. The present invention provides a reinforcing polymer suitable to withstand strain in one or more directions without leaking, and is well suited for medical devices and inflatable devices. The material is particularly well suited for catheter balloon applications requiring a small initial profile for entry into a vessel. The material is preferably stronger in a longitudinal direction as opposed to its transverse direction.

There are numerous porous membranes which would be suited to use for an imbibed polymer. As shown in the following examples, ePTFE has been used to demonstrate the present invention based upon preferred properties of thinness and drapability. While reinforcing polymers with anisotropic properties are preferred for embodiments such as catheter balloons, an isotropic reinforcing polymer may be desired for other imbibed material embodiments.

Figure 1B:
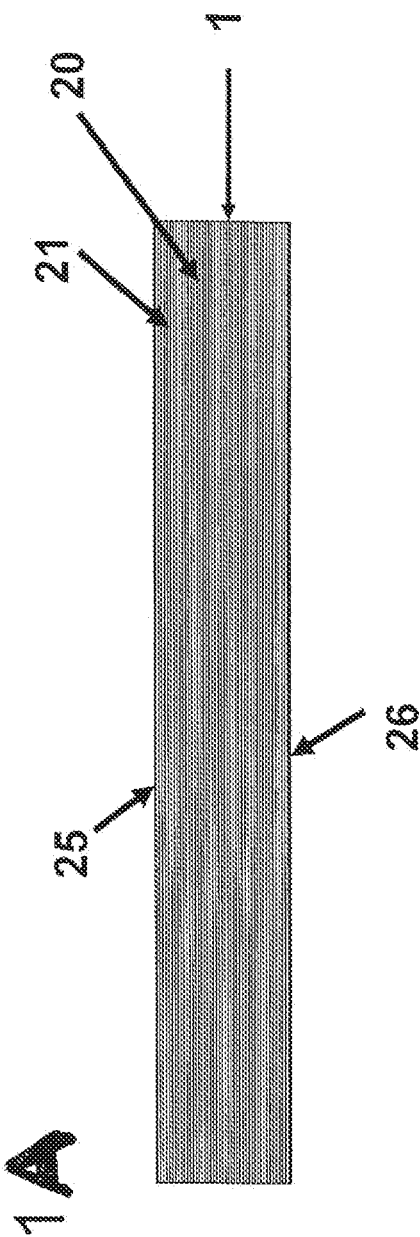
FIGS. 1A and 1B show cross sections of a reinforcing polymer.
Figure 1A:
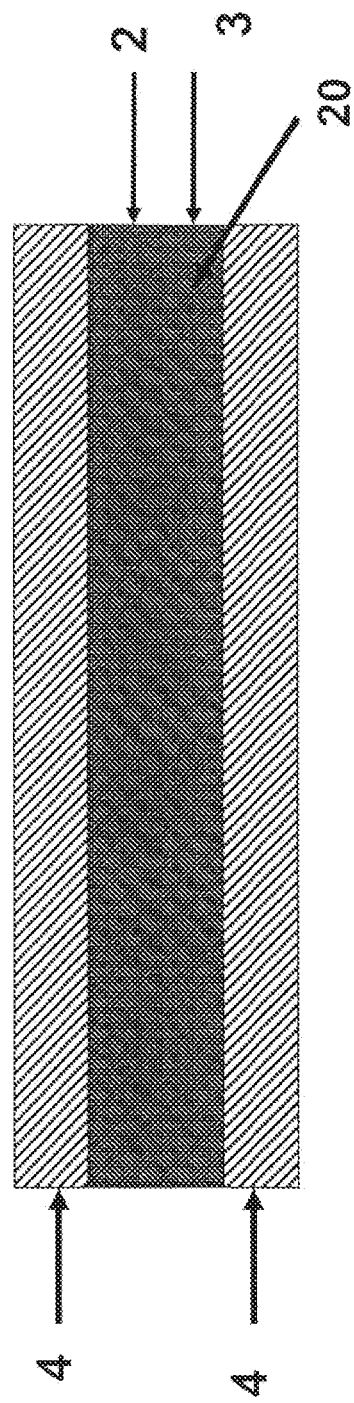
Figure 2:
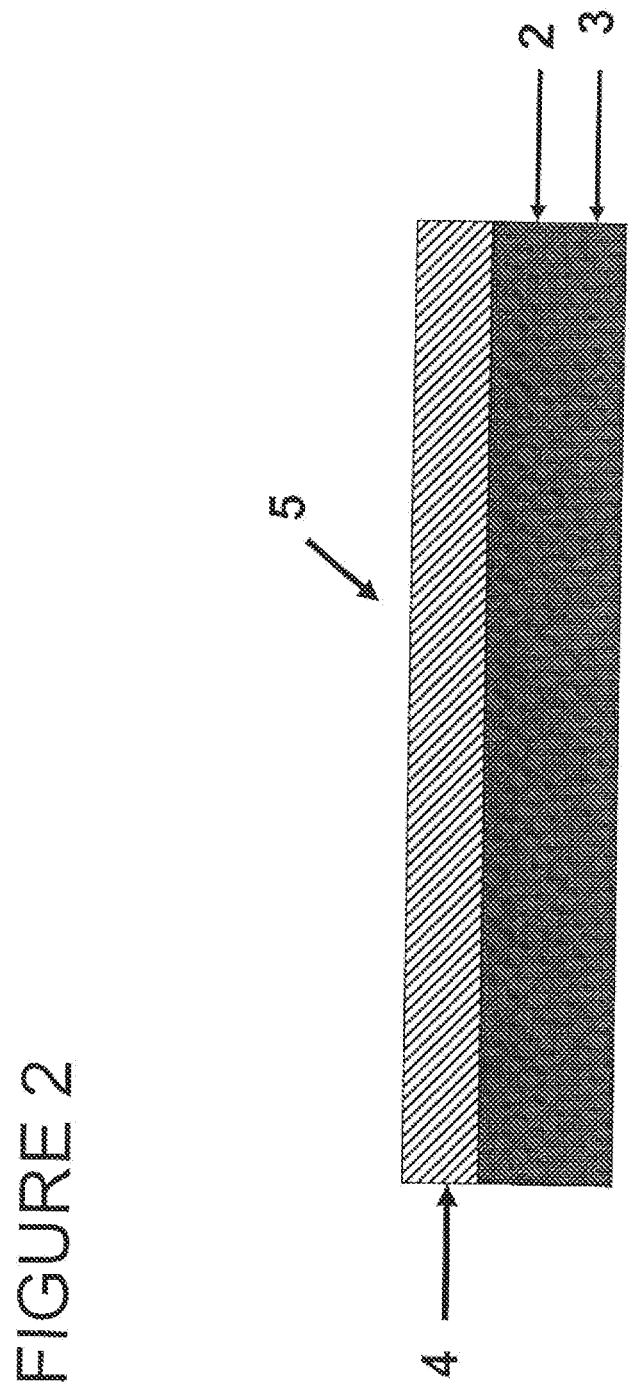
FIG. 2 shows a cross section of a reinforcing polymer with a single surface coating.

As shown in FIGS. 1A and 1B, the reinforcing polymer 1 comprises at least one matrix 20 with void spaces 21. The matrix should have a top side 25 and a bottom side 26. A sealing material 3 is imbibed into the reinforcing polymer 1 to form an imbibed reinforcing polymer 2. The sealing material 3 substantially seals the porous matrix void spaces 21 and extends beyond the reinforcing polymer matrix 20 to form a surface coating 4 on one side of the reinforcing polymer 1, as shown in FIG. 2; or both sides of the imbibed reinforcing polymer 2, as shown in FIG. 1A. The sealing material 3 must be of a sufficient quantity not only to seal void spaces in the reinforcing polymer, but to extend beyond the matrix of the reinforcing polymer and form a continuous layer as a surface coating 4. The surface coating forms a continuous layer that is free from holes and extends beyond the matrix of the reinforcing polymer. The reinforcing polymer may be comprised of any porous polymer, including but not limited to fluoropolymers, polyamides, polyesters, polycarbonates, microporous polyolefins, or UHMW polyurethanes. The matrix can be that of a form typical of any oriented matrix, including ePTFE.

The composite film of the present invention comprises a porous reinforcing layer and a continuous polymer layer. The porous reinforcing polymer layer is preferably a thin, strong porous membrane that can be made in sheet form. The porous reinforcing polymer can be selected from a group of polymers including, but not limited to, olefin, PEEK, polyamide, polyurethane, polyester, polyethylene, and polytetrafluoroethylene. In a preferred embodiment, the porous reinforcing polymer is anisotropic such that it is highly oriented in the one direction. An ePTFE membrane with a matrix tensile value in one direction of greater than 690 megapascals is preferred, and greater than 960 megapascals is even more preferred, and greater than 1,200 megapascals is most preferred. The exceptionally high matrix tensile value of ePTFE membrane allows the composite material to withstand very high hoop stress in the inflated balloon configuration. In addition, the high matrix tensile value of the ePTFE membrane makes it possible for very thin layers to be used which reduces the deflated balloon profile. A small profile is necessary for the balloon to be able to be positioned in small arteries or veins or orifices. In order for balloons to be positioned in some areas of the body, the balloon catheter must be able to move through a small bend radius, and a thinner walled tube is typically much more supple and capable of bending in this manner without creasing or causing damage to the wall of the vessel.

In another preferred embodiment, the ePTFE membrane is relatively mechanically homogeneous. The mechanically balanced ePTFE membrane can increase the maximum hoop stress that the composite film made therefrom can withstand.

The continuous polymer layer of the present invention is coated onto at least one side of the porous reinforcing polymer. The continuous polymer layer is preferably an elastomer, such as, but not limited to, aromatic and aliphatic polyurethanes including copolymers, styrene block copolymers, silicones, preferably thermoplastic silicones, fluorosilicones, fluoroelastomers, THV and latex. In one embodiment of the present invention, the continuous polymer layer is coated onto only one side of the porous reinforcing polymer. The continuous polymer layer is coated onto both sides of the porous reinforcing polymer. In a preferred embodiment, the continuous polymer layer is imbibed into the porous reinforcing polymer and the imbibed polymer fills the pores of the porous reinforcing polymer.

The continuous polymer layer can be applied to the porous reinforcing polymer through any number of conventional methods including, but not limited to, lamination, transfer roll coating, wire-wound bar coating, reverse roll coating, and solution coating or solution imbibing. In a preferred embodiment, the continuous polymer layer is solution imbibed into the porous reinforcing polymer. In this embodiment, the continuous polymer layer is dissolved in a suitable solvent and coated onto and throughout the porous reinforcing polymer using a wire-wound rod process. The coated porous reinforcing polymer is then passed through a solvent oven and the solvent is removed leaving a continuous polymer layer coated onto and throughout the porous reinforcing polymer. In some cases, such as when silicone is used as the continuous polymer layer, the coated porous reinforcing polymer may not require the removal of solvent. In another embodiment, the continuous polymer layer is coated onto at least one side of the porous reinforcing polymer and maintained in a "green" state where it can be subsequently cured. For example, an ultraviolet light (UV) curable urethane may be used as the continuous polymer layer and coated onto the porous reinforcing polymer. The composite film comprising the porous reinforcing polymer and the UV curable urethane continuous polymer layer can then be wrapped to form at least one layer of the balloon and subsequently exposed to UV light and cured. A pass is a number of layers applied in a wrapping event. A layer may comprise a single layer of composite film wrapped around the balloon.

Some typical examples of the reinforcing polymer can generally be found at U.S. Pat. No. 5,476,589 and U.S. patent application Ser. No. 11/334,243. The surface coating is of a sufficient thickness to maintain a watertight matrix when the sealing material is stressed, inflated, or strained. The sealing material 3 is typically an elastomeric polymer or viscous flow material, such as an elastomer, urethane, fluoropolymer, nylon, polyether block amide, PEBA, or other suitable material.

In one embodiment, a catheter balloon may be constructed which changes in diameter by up to 700 percent. During the diameter growth, the balloon wraps rotate towards the balanced force angle of about 54.7 degrees, while the elastomer imbibed reinforcing polymer will strain perpendicular to the wrap length up to 400-500 percent. This aspect is unique, the perpendicular strain caused by the rotation to the balanced force angle allows higher radial elongation of the balloon at less strain on the elastomer, as compared to a balloon created from the elastomer alone. This attribute of the present invention provides improved balloons with better recovery and which are of a higher strength and higher burst pressure than traditional balloons. Further, the diameter of the elastomer balloon may be formed to limit the diameter growth once the balanced forces angle is reached. This also allows for symmetrical inflation of the balloon.

The wrap layers when configured in accordance with the present invention form a balanced force angle which prevents the layers from incurring transverse strain as the balloon inflates. Transverse strain is the tendency for individual material layers to stretch or strain perpendicular to the wrap angle. For this reason, anisotropic materials are used which are highly oriented in the direction of the wrap angle to allow for the strain in the perpendicular direction. Additionally, the balloon exhibits essentially radial symmetry upon inflation. The balloon is wrapped by winding layers at opposing directions to one another until a desired thickness is obtained. The balloon material passes may be comprised of the same materials or different materials. While the thickness of the materials may vary, for vascular use it is advantageous to use balloon material that is less than 2 micrometers thick.

The following equation is useful for predicting the amount of transverse strain upon the elastomer imbibed reinforcing polymer during inflation of a balloon catheter of the present invention:

initial width/final inflated width=$1/(\cos \alpha_f/\cos \alpha_i)^2 \times (\tan \alpha_f/\tan \alpha_i)$ wherein α is defined as the angle between the longitudinal axis of the balloon and the angle of the wrapped elastomer imbibed reinforcing polymer.

Figure 3:
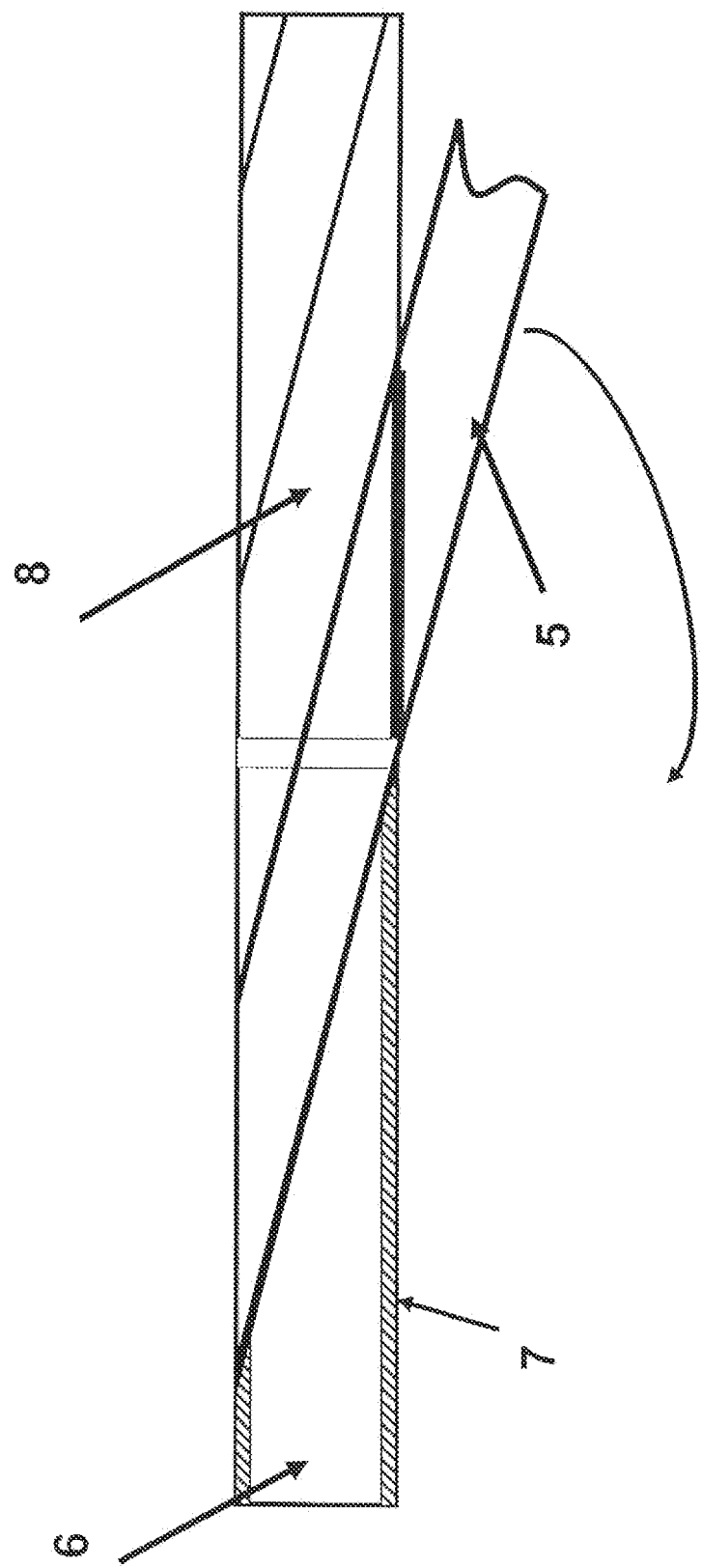
FIG. 3 shows a composite film wrapped at a low angle on a release coated core wire.
Figure 4:
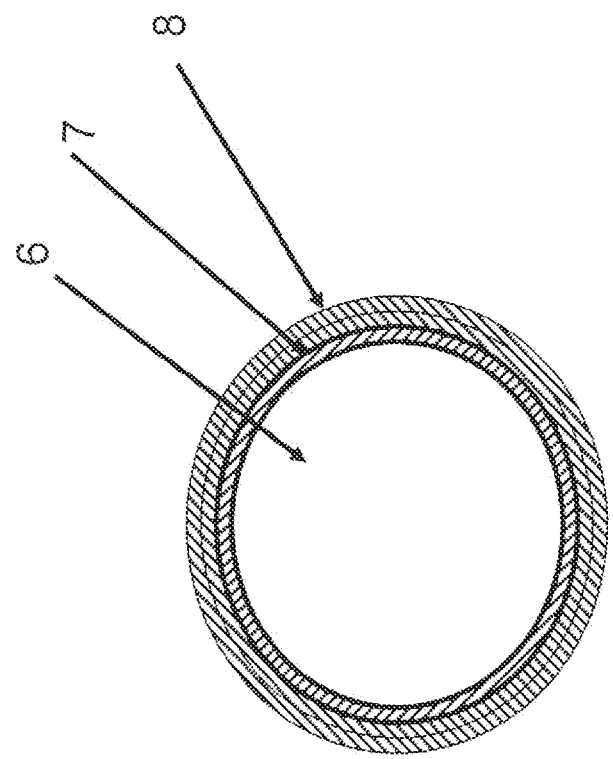
FIG. 4 shows a cross section of a balloon material layer wrapped on a wire.
Figure 5:
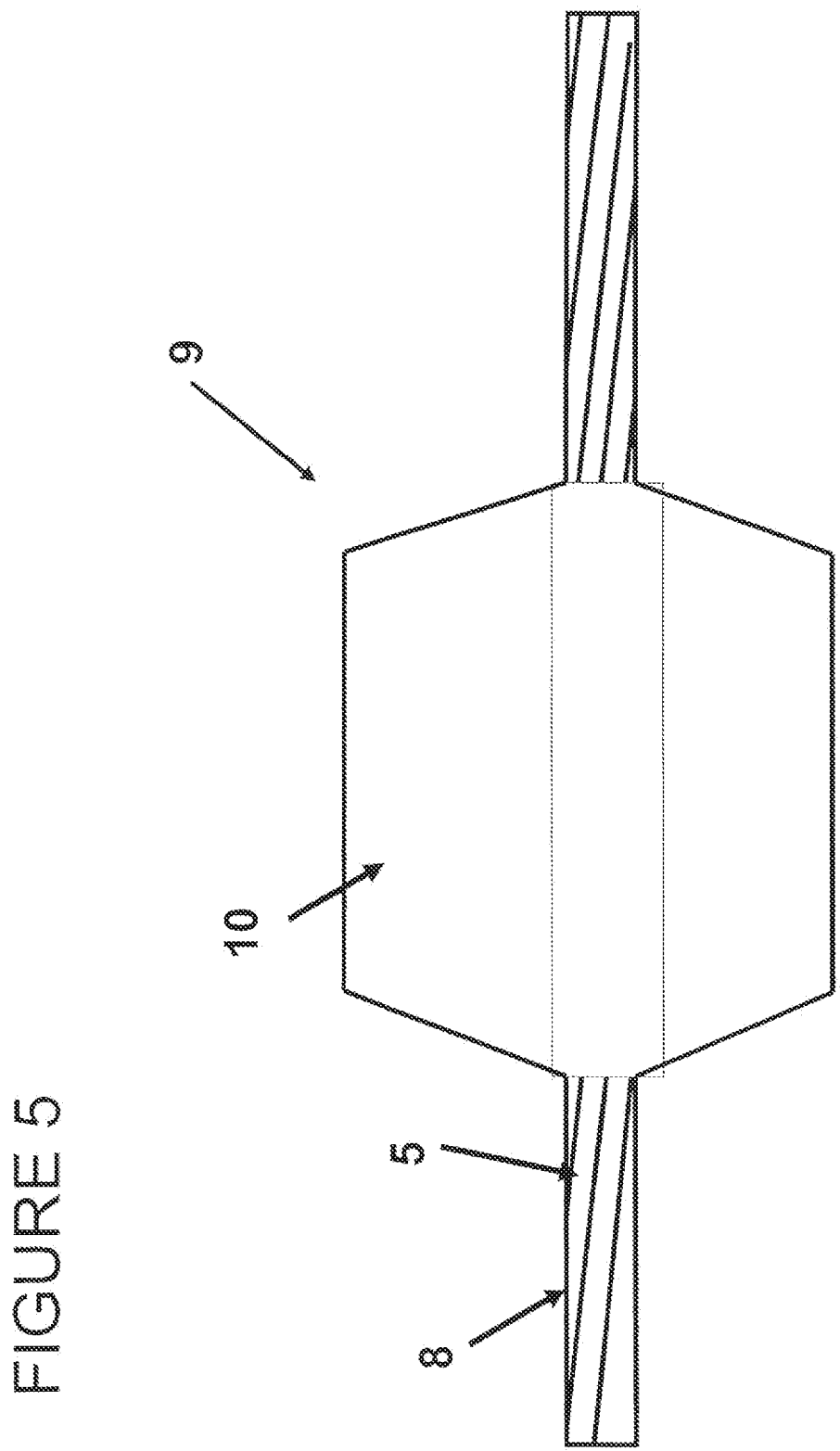
FIG. 5 shows a bladderless balloon with a heat treated inflation region.

In certain applications, it may be desirable that the surface coating is formed at a thickness which allows for controlled porosity when strained due to inflation. Such controlled porosity allows delivery of a liquid in therapeutic quantities. The combination of the surface coating 4 and the imbibed reinforcing polymer 2 provides a composite film 5. The composite film 5 has a surface coating possessing a greater strain capability than either the sealing material 3 or the reinforcing polymer 1 alone. In certain preferred embodiments it is desirable to use ePTFE as the reinforcing polymer 1. To produce a thin strong reinforcing polymer with a desired mass and thickness, the polymer is expanded longitudinally and transversely prior to imbibing with a sealing material 3. The longitudinal expansion ratio is greater than the transverse expansion ratio. As shown in FIG. 3, the composite film 5 of the present invention is suited for use as a balloon material layer 8. The composite film 5 can be cut or formed in longitudinal strips or narrower pieces suitable for wrapping the composite film around a core wire 6 or mandrel with or without a release coating 7. The angle of the wrap can vary depending upon the desired attributes of the finished balloon. Several different areas of differing wrap angles may exist on one balloon. In one desired embodiment the wrap angle of the composite film is between 2 and 54 degrees with respect to the longitudinal axis of the balloon, and more preferably less than ten degrees with respect to the longitudinal axis of the balloon. The composite film can be wrapped at an angle with respect to the longitudinal axis which promotes inflation to a defined diameter, then wrapped in a reverse direction at an opposing angle to the first pass for a plurality of passes forming directional layers. Upon inflation, the layers of opposing directions form a balanced force angle approaching 54 degrees relative to each other. As shown by the cross section in FIG. 4, the balloon material layer 8 can be wrapped in layers around the core wire 6 (or around a release coating 7 on the wire) to form a tubular structure suitable for use as an inflatable balloon when sealed at the ends. The tubular structure may be subjected to heat and inflation pressure to form a bladderless balloon with or without the use of a mold. The balloon of the present invention does not require a bladder, but may be constructed with a bladder if desired. In one embodiment the balloon is comprised of at least two helically oriented wrap layers which form an angle of approximately 54 degrees with respect to each other upon inflation. This angle allows the forces within the filament wound pressure vessel to be at equilibrium. The inflatable balloon of the present invention further exhibits radial symmetry upon inflation and non-foreshortening. By non-foreshortening it is meant that the length of the balloon does not change by more than ten percent (more preferably 5 percent and even more preferably 2 percent) upon inflation to a rated burst pressure. As shown in FIG. 5, the composite film 5 can be used as a balloon material layer 8 and formed into a bladderless balloon 9 suitable for use as a catheter. Upon inflation, the inflated region 10 expands into a predetermined shape.

Figure 6:
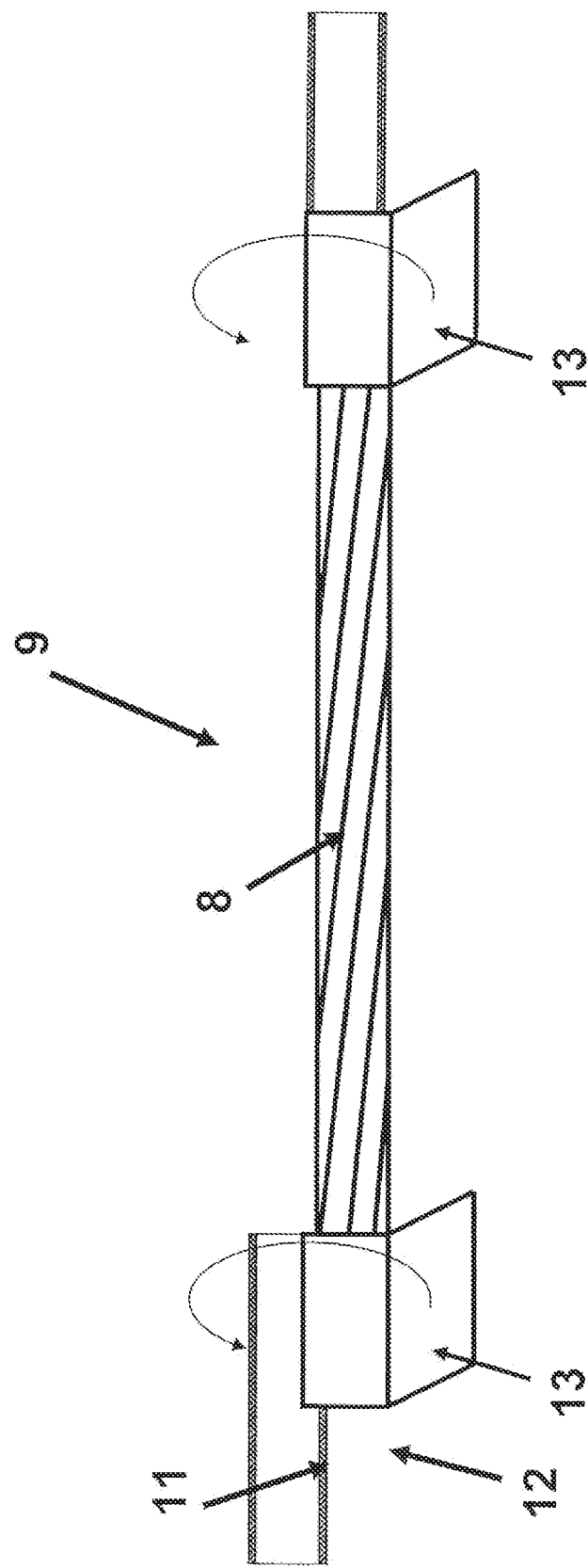
FIG. 6 shows a schematic diagram depicting attachment via two sealing means of a bladderless balloon to a hypotube.

FIG. 6 shows a balloon catheter device 9 with a bladderless balloon attached to a hypotube. The bladderless balloon is attached to the hypotube or catheter shaft via a seal or other sealing means 13. The material of the present invention may be used as the sealing means. For example in the present invention the sealing means holds the balloon material layer 8 in contact with the hypotube 11 so that the balloon may be inflated without pressure loss. The hypotube 11 has a longitudinal axis around which the inflatable balloon is affixed. The hypotube may further comprise a hypotube wrap layer 12 surrounding the hypotube. When the hypotube wrap layer is present, the balloon material is affixed to the hypotube wrap layer via a sealing means to form a seal.

Figure 7:
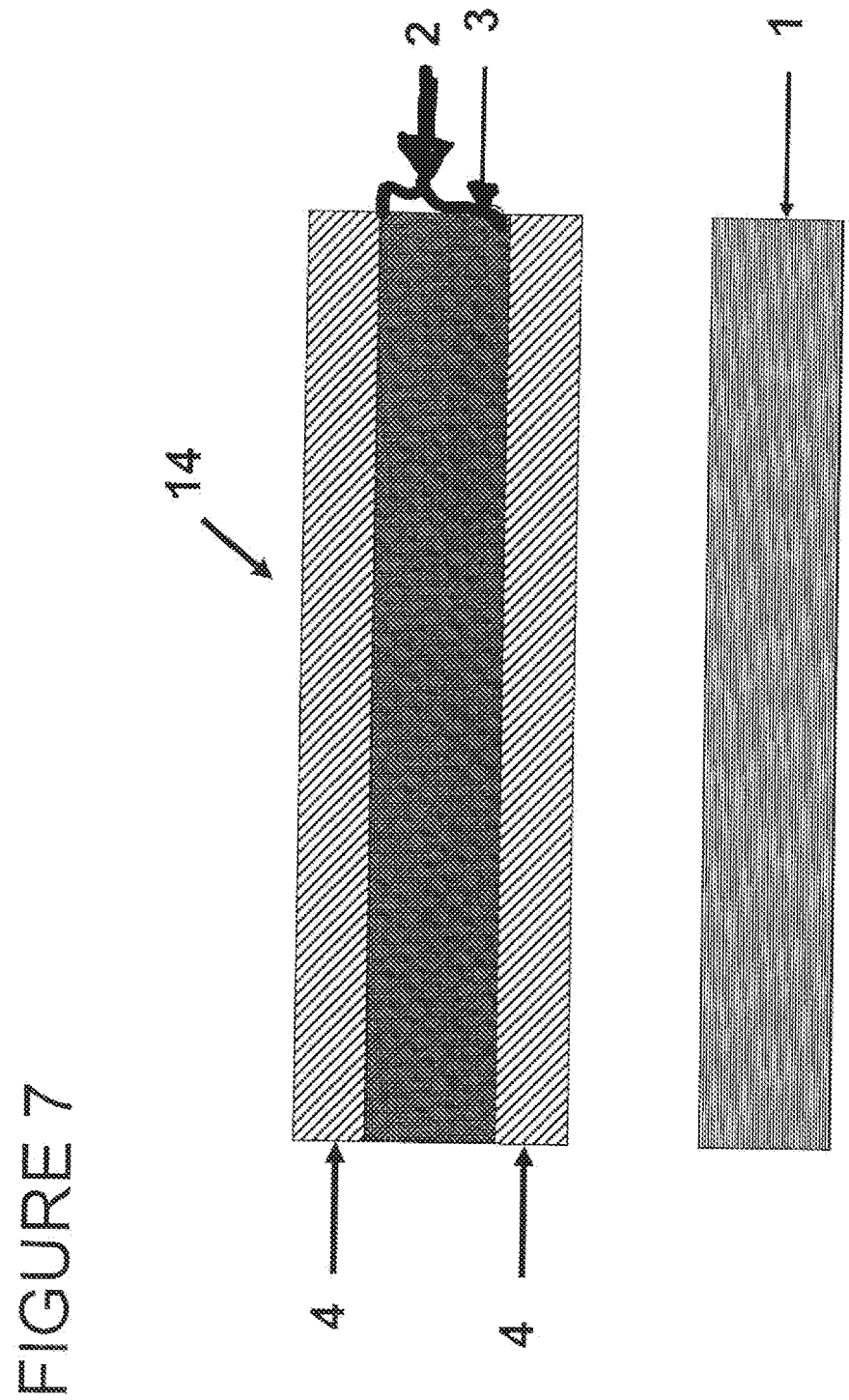
FIG. 7 shows a cross section of a single coated anisotropic material

FIG. 7 shows a reinforcing polymer 1 imbibed with a sealing material 3 to form an imbibed reinforcing polymer 2 having a double surface coating 4 layer, and forming a stretchable anisotropic material. A single surface coating may be used when only one side of the material wrap is desired to be coated. The surface coating may be present on the inside surface or the outside surface of the balloon.

Figure 8:
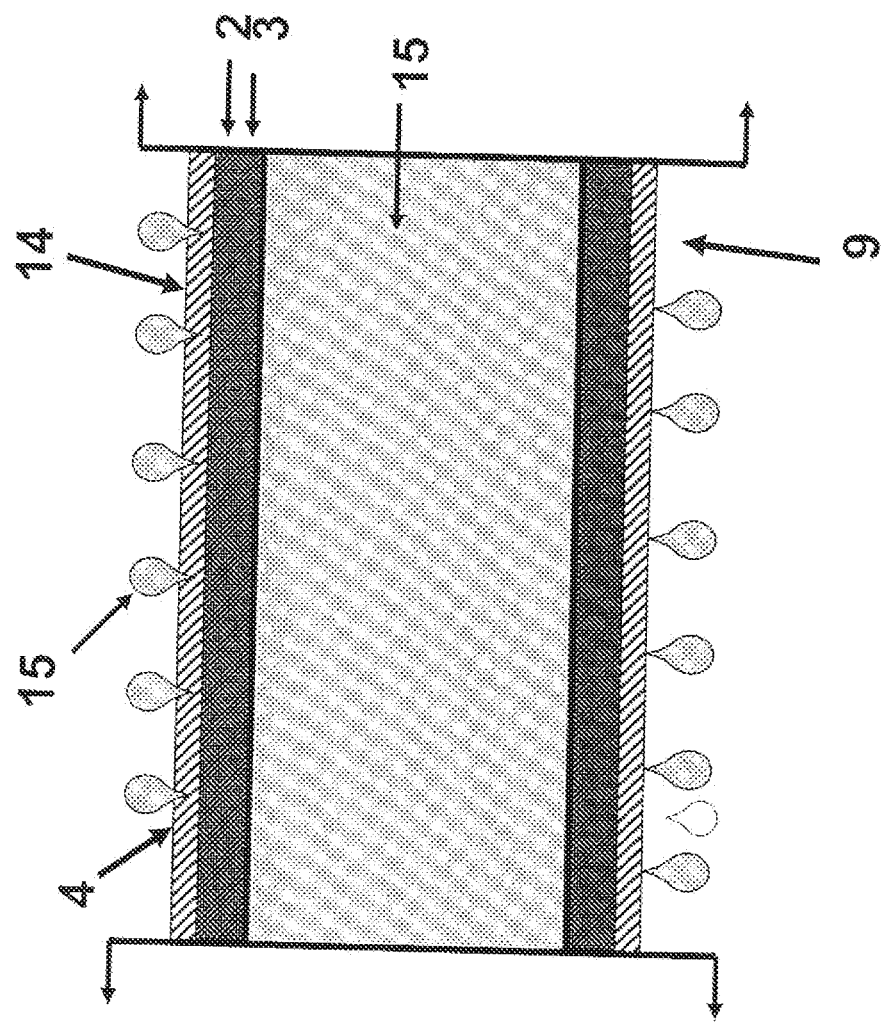
FIG. 8 shows a cross section of a bladderless balloon for fluid delivery at higher pressures.

In another embodiment, FIG. 8 shows a cross section of a bladderless balloon having a surface coating of a thickness allowing for controlled porosity when strained due to inflation. Controlled porosity allows delivery of a liquid 15 from one side of the imbibed reinforcing polymer to the other side. The controlled porosity is a tortuous path, thereby allowing the therapeutic liquid to weep, (form droplets on the surface of the balloon). In another embodiment, the bladderless balloon having a surface coating of a thickness allowing for controlled porosity, weeps only at high pressure. As shown in FIG. 8, the imbibed reinforcing polymer 2 has at least one surface coating 4 formed by the sealing material 3. The imbibed reinforcing polymer is formed into a bladderless balloon 9 having stretchable anisotropic material 14 properties. When the bladderless balloon is inflated by a fluid, small openings occur in the surface coating which allow movement of the fluid from the interior side of the balloon through the imbibed reinforcing polymer 2 to the outside of the balloon. Delivery of therapeutic liquid agents may be facilitated using a bladderless balloon comprised of an imbibed reinforcing polymer with a controlled porosity. This controlled porosity is able to withstand pressures greater than 10 p.s.i., before allowing fluid movement from the interior to the exterior side of the balloon.

Figure 9:
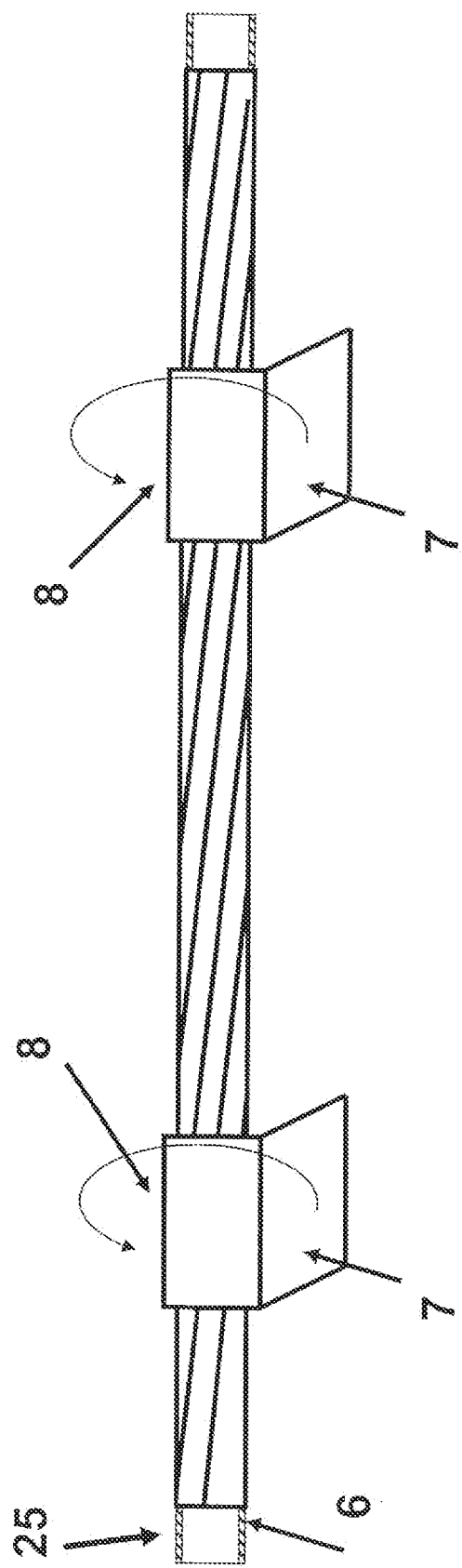
FIG. 9 shows non-distensible seal wrapped onto a balloon material layer.

FIG. 9 shows that the bladderless balloon may be constructed to include at least one non-distending layer 7 to provide a desired shape to the bladderless balloon or to provide a continuous integrated seal on an inflatable balloon. The continuous integrated seal may be formed by using or providing a first balloon material layer 8 which is configured to form a desired balloon shape. The sealing material may be a balloon material layer 8, as such, an ePTFE reinforcing polymer imbibed with sealing material 3. The balloon shape is then wrapped with a wrap layer around said first balloon material layer so that the angle of the wrap changes to wrap at least one wrap layer at an angle sufficient to create seal over the first balloon material layer upon inflation. A second balloon material layer may then be wrapped around the seal to increase the bonding surface area of the seal if desired. In this manner the seal is located between two balloon materials to provide a gentle failure mode on a bladderless balloon. The material composite may be used to comprise the non-distensible regions. As shown in FIG. 9, the core wire 6 may be provided with a release coating 25. The release coating may be of a desired thickness to provide a desired inner diameter on the finished balloon. The release coating has a balloon material layer wrapped and set around the core wire 6 to provide a bladderless balloon.

Figure 10:
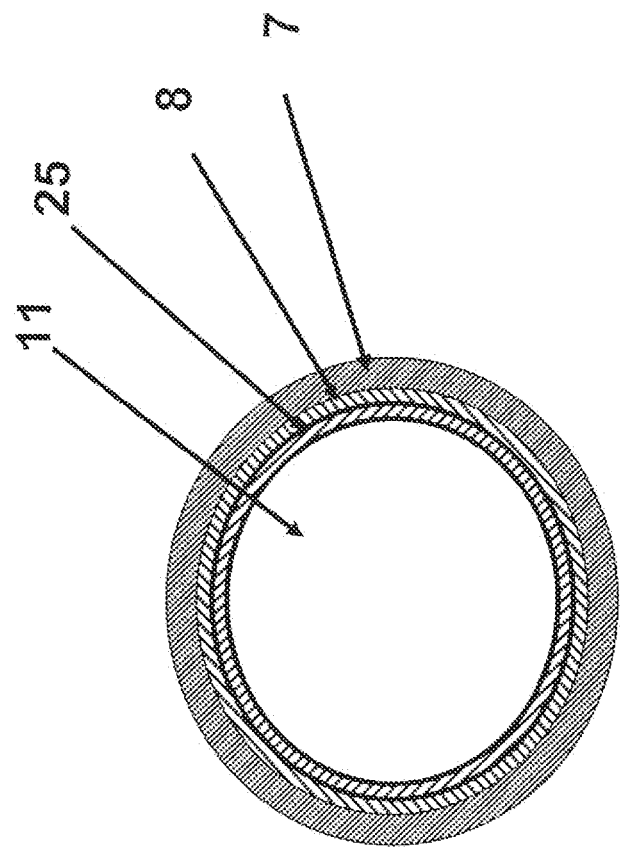
FIG. 10 shows a cross section of a non-distensible seal wrapped onto a balloon material layer.

FIG. 10 provides a cross section of a non-distensible seal on a bladderless balloon. The non-distensible seal is integrated as a wrap layer on top of the balloon itself. It may be wrapped at the same time as the bladderless balloon by adjusting the wrap angle of the composite film wrap. The balloon material layer 8 is then wrapped with a non-distending layer 7 in desired areas to provide the bladderless balloon with non-distending regions, as shown in FIG. 9. The non-distending regions should be comprised of balanced multiple wrap layers oriented so that the number of passes of wrap lying in one direction is equal to the number of passes of wrap in an opposite overlying direction.

The following examples are offered for illustrative purposes only and are not intended to limit the teaching of the present invention.

EXAMPLES

Example 1—Composite Film

The ePTFE reinforcing polymer 1 used to make the composite film was made in accordance with the teachings found in U.S. Pat. No. 5,476,589 to Bacino, incorporated by reference herewith. Specifically, the ePTFE reinforcing polymer was longitudinally expanded to a ratio of 55 to 1 and transversely expanded approximately 2.25 to 1, to produce a thin strong reinforcing polymer with a mass of approximately 3.5 g/m² and a thickness of approximately 6.5 micrometers.

The composite film 3 was made by using a wire-wound rod coating process whereby a solution of Tecothane TT-1085A polyurethane (Thermedics, Inc., Woburn, Mass.) and tetrahydrofuran (THF) was coated onto an ePTFE reinforcing polymer. A 3-8 percent by weight solution of Tecothane TT-1085A polyurethane in THF was coated onto the ePTFE reinforcing polymer to produce a composite film with approximately equal amounts of Tecothane TT-1085A polyurethane as depicted in FIG. 1B on either side and throughout the ePTFE reinforcing polymer and a total polymer weight application of approximately 40-60 percent of the total final composite film weight.

Example 2—Bladderless Balloon

The bladderless balloon of the present invention was made by wrapping a composite film of Techothane TT-1085A polyurethane (Thermedics, Inc., Woburn, Mass.), and ePTFE reinforcing polymer over a FEP coated silver-plated copper core wire (Putnam Plastics LLC, Dayville, Conn.). The wrapped core wire was heat treated and the center wire and FEP coating were subsequently removed to provide a hollow composite balloon tube.

The core wire was a 0.2 mm diameter silver-plated copper wire with a fluoroethylene-propylene (FEP) 5100 coating that resulted in a final wire diameter of 0.394 mm. The ePTFE reinforcing polymer used to make the composite film is described in Example 1. Specifically, the ePTFE reinforcing polymer was longitudinally expanded to a ratio of 55 to 1 and transversely expanded approximately 2.25 to 1, to produce a thin strong reinforcing polymer with a mass of approximately 3.5 g/m² and a thickness of approximately 6.5 micrometers.

The composite film was made by using a wire-wound rod coating process whereby a solution of Tecothane TT-1085A polyurethane and tetrahydrofuran (THF) was coated onto an ePTFE reinforcing polymer. A 3-8 percent by weight solution of Tecothane TT-1085A polyurethane in THF was coated onto the ePTFE reinforcing polymer to produce a composite film with approximately equal amounts of Tecothane TT-1085A polyurethane on either side and throughout the ePTFE reinforcing polymer and a total polymer weight application of approximately 40-60 percent of the total final composite film weight.

The composite film was slit to 5 mm wide and helically wrapped around the 30.5 cm long core wire at a 4 to 5 degree angle from the longitudinal axis of the wire. The wrapped core wire was heated for approximately 5 to 30 seconds at 180° C. after wrapping. The core wire was then wrapped with the composite film in the opposite direction at a 4 to 5 degree angle from the longitudinal axis of the wire and subsequently heated for approximately 5 to 30 seconds at 180° C. The process of wrapping the core wire in opposite directions and heating after each pass was repeated until a total of four passes of wrapping was complete. The wrapped core wire was wrapped around a pin frame with approximately 30 cm spaces between pins and approximately 180 degrees of wrap around each pin and tied at the ends before being placed into an oven and heated for approximately 30 minutes at 150° C.

The core wire and the FEP coating over the core wire were removed from the composite balloon over wire construction. An approximately 2.54 cm long section of the composite hollow balloon tube was removed from either end of a 30.5 cm long section of the balloon over wire construction. The exposed ends of the wire were clamped with hemostats and pulled by hand until the wire had been stretched approximately 5 cm, at which point it was removed from the center of the tube. The plastic FEP coating was removed in a similar fashion, but was stretched approximately 50 cm before it was removed from the balloon. A composite hollow balloon tube was produced with a first layer wrapping material at a low (4 to 5 degree) angle of wrap.

The 2.85 mm inflated diameter by 27 mm long balloon was mounted to a 0.36 mm diameter stainless steel hypotube (Creganna Medical Devices, Parkmore West Galway, Ireland) that had been helically wrapped with approximately three layers of expanded PTFE reinforcing polymer and EFEP fluoroplastic composite with the EFEP layer facing the stainless steel tube. The balloon was attached and sealed to the catheter shaft by wrapping an approximately 5 mm wide ePTFE/eFEP film circumferentially around the balloon approximately five times. One band was wrapped on each end of the balloon and was centered over the end of the balloon and the catheter such that it made a seal by contacting both the hypotube shaft and the balloon as depicted in FIG. 6.

Example 3—Bladderless Balloon with Heat Inflation Technique

The bladderless balloon of the present invention was made by wrapping a composite film of Techothane TT-1085A polyurethane (Thermedics, Inc., Woburn, Mass.), and ePTFE reinforcing polymer over a FEP coated silver-plated copper core wire (Putnam Plastics LLC, Dayville, Conn.). The wrapped core wire was heat treated and the center wire and FEP coating were subsequently removed to provide a hollow composite balloon tube.

The core wire was a 0.2 mm diameter silver-plated copper wire with a fluoroethylene-propylene (FEP) 5100, coating that resulted in a final wire diameter of 0.394 mm. The ePTFE reinforcing polymer was longitudinally expanded to a ratio of 55 to 1 and transversely expanded approximately 2.25 to 1, to produce a thin strong reinforcing polymer with a mass of approximately 3.5 g/m$^2$ and a thickness of approximately 6.5 micrometers.

The composite film was made by using a wire-wound rod coating process whereby a solution of Tecothane TT-1085A polyurethane and tetrahydrofuran (THF) was coated onto an ePTFE reinforcing polymer. A 3-8 percent by weight solution of Tecothane TT-1085A polyurethane in THF was coated onto the ePTFE reinforcing polymer to produce a composite film with approximately equal amounts of Tecothane TT-1085A polyurethane on either side and throughout the ePTFE reinforcing polymer and a total polymer weight application of approximately 40-60 percent of the total final composite film weight.

The composite film was slit to 5 mm wide and helically wrapped around the 30.5 cm long core wire at a 4 to 5 degree angle from the longitudinal axis of the wire. The wrapped core wire was heated for approximately 5 to 30 seconds at 180° C. after wrapping. The core wire was then wrapped with the composite film in the opposite direction at a 4 to 5 degree angle from the longitudinal axis of the wire and subsequently heated for approximately 5 to 30 seconds at 180° C. The process of wrapping the core wire in opposite directions and heating after each pass was repeated until a total of four passes of wrapping was complete. The wrapped core wire was wrapped around a pin frame with approximately 30 cm spaces between pins and approximately 180 degrees of wrap around each pin and tied at the ends before being placed into an oven and heated for approximately 30 minutes at 150° C.

The core wire and the FEP coating over the core wire were removed from the composite balloon over wire construction. An approximately 2.54 cm long section of the composite hollow balloon tube was removed from either end of a 30.5 cm long section of the balloon over wire construction. The exposed ends of the wire were clamped with hemostats and pulled by hand until the wire had been stretched approximately 5 cm, at which point it was removed from the center of the tube. The plastic FEP coating was removed in a similar fashion, but was stretched approximately 50 cm before it was removed from the balloon. A composite hollow balloon tube was produced with a first layer wrapping material at a low (4 to 5 degree) angle of wrap.

A 15.25 cm long section of the composite hollow balloon tube was tied into a knot and clamped with a hemostat on one end. The opposite end was slipped through a Qosina male tuohy borst with spin lock fitting (#80343, Qosina Corporation, Edgewood, N.Y.), and a Monoject blunt needle with Aluminum luer lock hub (model #8881-202389, Sherwood Medical, St. Louis, Mo.) was inserted approximately 2.0 cm into the balloon. The hemostatic valve was tightened to seal the balloon, and was then attached to a Balloon Development Station Model 210A (Beahm Designs, Inc., Campbell, Calif.). The nozzle airflow was set to 25-30 units and the temperature was set to 140° C., air pressure to 2.58 atmospheres. The air pressure was turned on, the center 40 mm long region to be inflated was subjected to heat for about 2-3 minutes resulting in a balloon with a diameter of 2.85 mm. The diameter was checked with a Mitutoyo Laser Scan Micrometer Model LSM-3100 (Mitutoyo America Corp, Aurora, Ill.) while in the inflated state. The resulting balloon had a diameter of 2.85 mm and an inflated length of 27 mm.

Using a Monoject blunt needle with Aluminum luer lock hub (model #8881-202389, Sherwood Medical, St. Louis, Mo.) dispensing needle, the balloon was subjected to an internal pressure of 5.44 atmospheres at room temperature for approximately 1 hour.

The 2.85 mm inflated diameter by 27 mm long balloon was mounted to a 0.36 mm diameter stainless steel hypotube (Creganna Medical Devices, Parkmore West Galway, Ireland) that had been helically wrapped with approximately three layers of expanded PTFE reinforcing polymer and EFEP fluoroplastic composite with the EFEP layer facing the stainless steel tube. The balloon was attached and sealed to the catheter shaft by wrapping an approximately 5 mm wide ePTFE/eFEP film circumferentially around the balloon approximately five times. One band was wrapped on each end of the balloon and was centered over the end of the balloon and the catheter such that it made a seal by contacting both the hypotube shaft and the balloon.

Example 4—Material Properties

All of the experimental runs were performed using Mayer Bar coating technology and direct solution feed to the coating surface.

The Mayer Bar is simply a metal bar with wire windings.

Bars with windings of different wire sizes are used to achieve the desired thickness in coating. The Mayer Bar is used to apply the wet coating to the ePTFE membrane. The coating dries with the aid of an inline oven. The finished coated membrane receives a second coat directly to the membrane surface. This process provides an even coating and offers flexibility in the laydown design.

Example 5

The Tecothane 1085 (TT1085) elastomer, used in the coating, is readily solvated in Tetrahydofuran (THF). THF is characterized by a low vapor pressure, and as expected, a fast evaporation rate. Using this material the following results were obtained:

Test Samples:
  Sample 1 Single Sided Coat "2 Passes"
  Sample 2 Single Sided Coat "4 Passes"
  Sample 3 Double Sided Coat "2 Passes"
  Sample 4 Double Sided Coat "4 Passes"
Results: Gross Testing @ Ambient Temperatures:
  Sample 1: Inflated to 30 atm—no weeping for two minutes.
  Sample 2: Inflated to 30 atm—no weeping for three minutes.
  Sample 3: Inflated to 30 atm—no weeping observed until burst at 3 minutes.

Sample 4: Inflated to 30 atm—no weeping observed until burst at 7 minutes.

Multiple Inflation Testing:

The following procedure was used for this test. Each unit was preconditioned at 37° C. for 2 minutes. At 37° C., nine inflations were made to 18 atm and held for 30 seconds. On the $10^{th}$ inflation, the unit was removed from the bath, wiped off, and inspected for weeping.

Sample 1: Weeping observed on the $10^{th}$ inflation.

Sample 2: Weeping observed on the $10^{th}$ inflation.

Sample 3: No weeping observed on $10^{th}$ inflation. Balloon was pressurized for 4 minutes.

Sample 4: No weeping observed on $10^{th}$ inflation. Balloon was pressurized for 45 minutes.

While particular embodiments of the present invention have been illustrated and described herein, the present invention should not be limited to such illustrations and descriptions. It should be apparent that changes and modifications may be incorporated and embodied as part of the present invention within the scope of the following claims.

The invention claimed is:

1. A medical device comprising:
an inflatable element including a composite membrane having a reinforcing layer and a polymer layer over the reinforcing layer, the reinforcing layer including a material having a porous microstructure, the polymer layer being formed by adding a polymeric material to the reinforcing layer such that the polymeric material is incorporated into the microstructure of the reinforcing layer and such that the polymeric material forms a coating on the reinforcing layer to define the polymer layer,
the inflatable element being a balloon that is configured to inflate to a working diameter in response to introduction of a fluid into the balloon at pressures greater than a designated pressure before allowing fluid movement from an interior side to an exterior side of the balloon.

2. The balloon of claim 1, wherein the fluid is a gas.

3. The balloon of claim 1, wherein the fluid is a liquid.

4. The medical device of claim 1, wherein the porous microstructure of the reinforcing layer includes a plurality of nodes and fibrils.

5. The medical device of claim 1, wherein the reinforcing layer includes ePTFE.

6. The medical device of claim 1, wherein the polymeric material is an elastomeric material.

7. The medical device of claim 6, wherein the elastomeric material is a polyether block amide.

8. The medical device of claim 1, wherein the polymeric material is a nylon.

9. The medical device of claim 1, wherein the polymeric material is imbibed into the microstructure of the reinforcing layer.

10. The medical devie of claim 1, wherein the composite membrane comprises a tubular structure.

11. The medical device of claim 10, wherein the tubular structure comprises sealed ends.

12. The medical device of claim 1, where in the inflatable element is mounted on an elongate member.

* * * * *

UNITED STATES PATENT AND TRADEMARK OFFICE
CERTIFICATE OF CORRECTION

PATENT NO. : 10,881,840 B2
APPLICATION NO. : 15/882653
DATED : January 5, 2021
INVENTOR(S) : Alex R. Hobson et al.

It is certified that error appears in the above-identified patent and that said Letters Patent is hereby corrected as shown below:

In the Claims

Column 12, Line 24, Claim 10 "devie" should read --device--.
Column 12, Line 28, Claim 12 "where in" should read --wherein--.

Signed and Sealed this
Seventh Day of December, 2021

Drew Hirshfeld
*Performing the Functions and Duties of the
Under Secretary of Commerce for Intellectual Property and
Director of the United States Patent and Trademark Office*